United States Patent [19]

Hubelbank et al.

[11] Patent Number: 5,197,479
[45] Date of Patent: Mar. 30, 1993

[54] AUTOMATIC ELECTRODE CHANNEL IMPEDANCE MEASUREMENT SYSTEM FOR EGG MONITOR

[75] Inventors: Mark Hubelbank, Sudbury; David Shadmon, Brookline, both of Mass.; Mark J. Leverault, Derry, N.H.

[73] Assignee: Mortara Instrument, Milwaukee, Wis.

[21] Appl. No.: 699,483

[22] Filed: May 13, 1991

[51] Int. Cl.$^5$ ............................................. A61B 5/04
[52] U.S. Cl. .................................. 128/696; 128/734; 128/419 PT
[58] Field of Search .......... 128/696, 710, 734, 419 PT

[56] References Cited

U.S. PATENT DOCUMENTS

| | | | |
|---|---|---|---|
| 3,566,233 | 2/1971 | Kahn et al. | 128/734 X |
| 4,141,351 | 2/1979 | James et al. | 128/696 |
| 4,245,643 | 1/1981 | Benzing et al. | 128/419 PT |
| 4,274,419 | 6/1981 | Tam et al. | 128/639 |
| 4,321,932 | 3/1982 | Francis | 128/696 |
| 4,337,776 | 7/1982 | Daly et al. | 128/419 PT |
| 4,577,639 | 3/1986 | Simon et al. | 128/696 X |
| 4,785,812 | 11/1988 | Pihl et al. | 128/419 D |
| 4,870,341 | 9/1989 | Pihl et al. | 128/734 X |
| 4,899,750 | 2/1990 | Ekwall | 128/734 X |
| 4,917,099 | 4/1990 | Stice | 128/696 |
| 4,993,423 | 2/1991 | Stice | 128/696 |
| 5,020,541 | 6/1991 | Marriott | 128/696 X |

OTHER PUBLICATIONS

A. J. Crawford and P. D. Smith, A Micropower Impedance Meter For Measuring Electrode Contact Impedance, J. of Biomed Engrg. vol. 1, No. 2, Apr. 1979.
VLSI in Holter Monitoring, VLSI Electronics: Microstructure Science, vol. 17 Chapter 6, p. 129-134, by Mark Hubelbank, Academic Press, Inc., 1989.

Primary Examiner—Lee S. Cohen
Assistant Examiner—Jeffrey R. Jastrzab
Attorney, Agent, or Firm—Foley & Lardner

[57] ABSTRACT

An impedance measurement system for electrocardiographic recorders which allows measurement of the electrode channel impedance without the need for a separate piece of equipment. The impedance measurement system, which is an integral part of the recorder, applies complementary oscillating currents having short transition times to an electrode channel defined by a pair of electrode leads, a pair of electrodes and the patient tissues. The analog current signals flowing through the electrode channel create a voltage across the electrode channel which is amplified and applied to a dual range filtering stage. The low range section of the dual range filtering stage generates a time-dependent signal which causes the output of the low range filtering circuit to produce a signal applied to the timing input of a microprocessor. The microprocessor calculates the time elapsed between each transition of the oscillating current signals and the occurrence of a signal at the output of the low range filtering circuitry. From that elapsed time, the microprocessor calculates the impedance of the electrode channel being monitored. In addition, in response to the signal appearing at the output of the high range section of the dual range filtering stage, the microprocessor verifies contemporaneously the integrity of the electrode leads in order to validate the measured impedance value.

8 Claims, 10 Drawing Sheets

AUTOMATIC ELECTRODE CHANNEL IMPEDANCE MEASUREMENT SYSTEM FOR EGG MONITOR

BACKGROUND OF THE INVENTION

The present invention relates to electrocardiographic recorders adapted to ascertain whether the impedance of an electrode channel defined by a pair of electrode leads, a pair of electrodes and the patient's tissues is suitably low to provide reliable recording of physiological signals. In particular, the present invention relates to a system for providing data to assist in determining whether medical electrodes are correctly applied to a patient's skin and in controlling the integrity of electrode leads.

It is commonly accepted that an important requirement for accurate and reliable electrocardiographic recording of subcutaneous electrical signals is that the impedance of the electrode channel from a recorder through a patient's tissues be as low as possible. This requires that each electrode be correctly attached to the patient's skin so that the interface impedance between the electrode and surrounding skin area is as low as possible. This also means that the electrical path from the recorder to the electrode be highly conductive. Research has shown that low level electrode channel impedance cannot be reliably determined by visually inspecting the quality of physiological signals generated at the beginning of a recording.

It is therefore necessary to measure the electrode channel impedance at the time the electrodes are applied to the patient's body to confirm that the impedance of the electrode channel is suitably low for reliable recording. Since medical electrodes tend to deteriorate over time, a precise confirmation of a low level electrode channel impedance at the beginning of the test becomes particularly important in Holter recordings where the electrodes must function accurately for 24 to 72 hours. As described in the article by A. J. Crawford and P. D. Smith, *A Micropower Impedance Meter for Measuring Electrode Contact Impedance*, J. of Biomed. Engrg. Vol. 1, No. 2, April 1979, generally, measurement of this impedance is done by injecting a low level current (usually a few microamps), generated by a constant current source, through the electrode channel and by measuring the resulting electrical potential across that electrode channel. Since the injected current remains constant over the range of impedances to be measured, the resulting voltage it generates across the electrode channel is directly proportional to the electrode channel impedance. Accordingly, it is possible to express the electrode channel voltage directly in terms of the corresponding electrode channel impedance value.

To avoid undesirable polarization effects, it is, however, preferable for the injected current to be an alternating current. The resulting voltage across the electrode channel is then amplified and filtered in order to display the impedance value of the electrode channel on a measuring instrument. However, because electrode channel impedance is frequency dependent (as it includes resistive and reactive components), it becomes necessary for the frequency of the applied alternating current to be in the typical range of physiological signals. This will assure that the impedance measured by injecting the alternating current is representative of that seen by the electrical circuit during actual recording of the physiological signals.

Thus, it is apparent that to make sure such conventional impedance measuring circuitry is able to determine with an acceptable degree of reliability the impedance of an electrode channel, some precautions must be taken. More particularly, the bandwidths of the signal conditioning circuitry and of the measuring instrument must be adapted to accurately measure the electrical potential across the electrode channel at physiological frequencies. Or, if it is preferable to use a panel meter of a type commercially available, additional rectification circuitry cooperating with a more commonly available meter will be required.

It is known that conventional methods of electrode impedance measurement such as those described above use a measuring instrument separate from the recording equipment. These "stand-alone" instruments are often powered by battery packs. As a result, additional circuitry may also be necessary to monitor the condition of these battery packs as a battery of substandard condition could undesirably affect the constant current level supplied to the electrode channel.

From the above, it is apparent that measuring electrode channel impedance with commonly available equipment presents serious limitations. More specifically, a separate piece of equipment with dedicated signal conditioning and monitoring circuitry and adapted measuring panel meter or rectification components is required.

Presently available recorders of physiological signals do not incorporate the capability to provide measurement of electrode channel impedance. As a result, an additional piece of equipment must be used in conjunction with the recorder in an environment where space is often already lacking. Moreover, in addition to the space limitation problem, such impedance measuring equipments commonly require dedicated analog circuitry consisting of a constant current source, signal amplification and filtering circuitry, a separate meter of adequate bandwidth or a more readily available meter associated with AC rectification circuitry, and components to monitor battery condition.

SUMMARY OF THE INVENTION

In view of the foregoing, it is a general aim of the present invention to provide an impedance measurement device not subject to the limitations of the prior art and suitable for combination with an electrocardiographic pace detect recorder.

Accordingly, it is an object of the present invention to provide an impedance measurement system which does not require an additional piece of equipment with considerable circuitry, but which instead is an integral part of a recorder of physiological signals.

An additional object of the present invention is to provide an impedance measurement system which shares circuitry with that used for recording physiological signals in order to reduce overall power consumption and space requirements.

It is another object of the present invention to provide an impedance measurement system which can alert the technician conducting the test of an inadequate application of the electrodes to the skin of the patient and/or of a defective electrode lead.

A further object of the present invention is to provide a method of measuring the impedance of an electrode channel using a measuring system having such properties.

It is yet another object of the present invention to provide a recorder of physiological signals capable of automatically determining whether two or three sets of electrode leads are connected to the patient, i.e., whether the recorder is set up to operate as a standard three channel recorder or as a two channel recorder with pace detect capability.

Other objects and advantages of the present invention will become apparent from the detailed description given hereinafter. It should be understood, however, that the detailed description and specific embodiments are given by way of illustration only, since, from this detailed description, various changes and modifications within the spirit and scope of the invention will become apparent to those skilled in the art.

BRIEF DESCRIPTION OF THE DRAWINGS

A preferred exemplary embodiment of an impedance measurement system in accordance with the invention will hereinafter be described in conjunction with the appended drawings wherein like designations denote like elements, and.

DETAILED DESCRIPTION OF A PREFERRED EXEMPLARY EMBODIMENT

Figure 1:
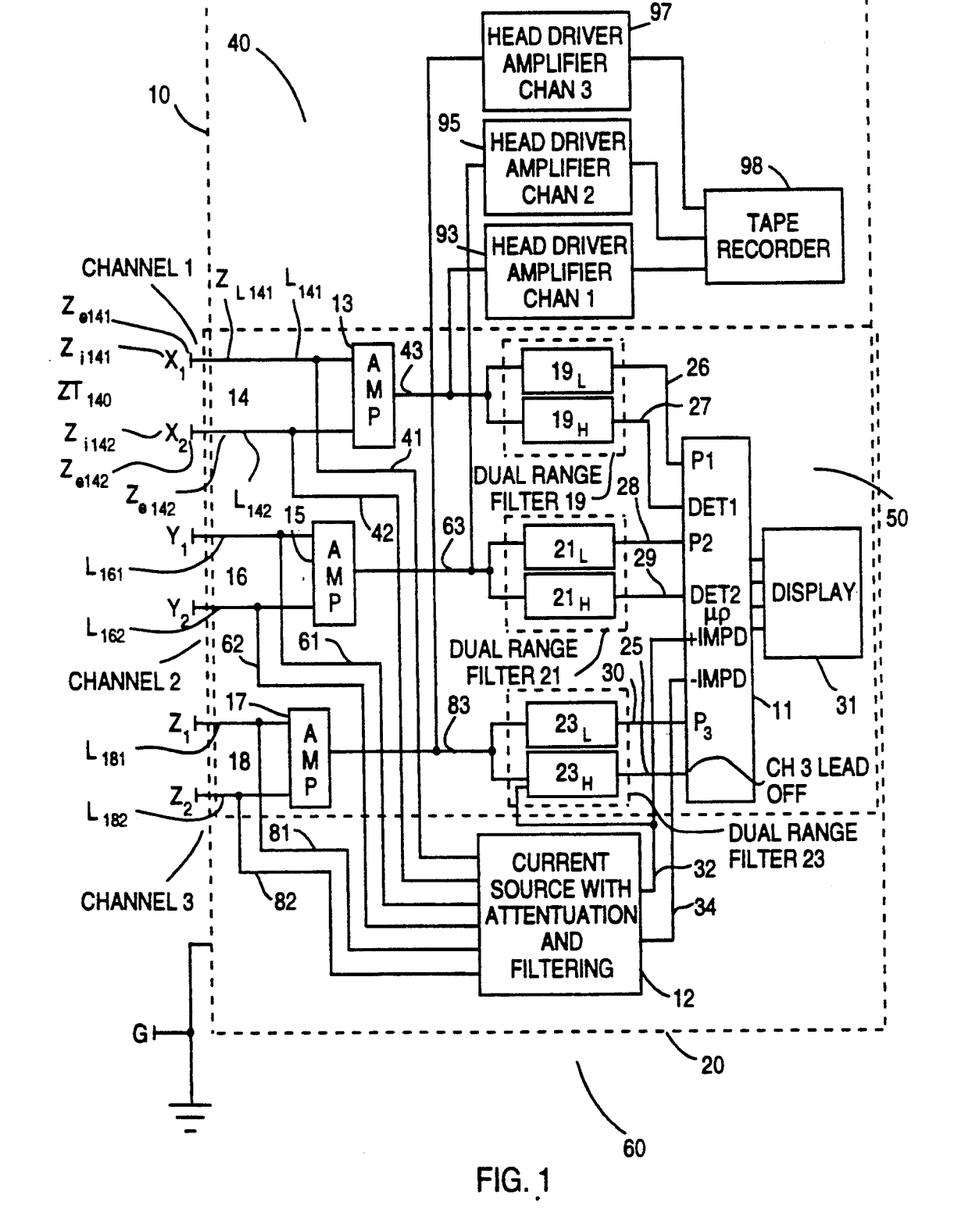
FIG. 1 is a schematic block diagram of an exemplary impedance measurement system 20 in accordance with the present invention cooperating with a conventional electrocardiographic pace detect recorder 10.

Turning now to the drawings, FIG. 1 illustrates a pace detect recorder 60 in accordance with the present invention which includes an impedance measurement system 20 cooperating with a conventional pace detect recorder 10.

Pace detect recorder 10, includes a recorder 40, such as Mortara Instrument model PR-3, comprising amplification stages 13, 15, 17, head driver amplifiers 93, 95, 97, and tape recorder 98. Conventional pace detect recorder 10 also includes conventional pace detect circuit 50 allowing detection of pacemaker signals contemporaneously with electrocardiographic recording. Conventional pace detect circuit 50 which includes circuitry commonly found in pace detect recorders advantageously includes microprocessor 11, dual range filtering stages 19, 21, and 23, and display 31.

Impedance measuring system 20 which is an integral part of pace detect recorder 60 preferably comprises appended current source 12 which cooperates with certain stages conveniently shared, without alteration, with pace detect recorder 10. Specifically, the circuitry which is shared by both pace detect recorder 10 and impedance measurement system 20 includes amplification stages 13, 15, 17, dual range filtering stages 19, 21, 23, microprocessor 11 and display 31.

Three pairs of electrodes, X1-X2, Y1-Y2, Z1-Z2 applied to a patient's body (not shown) are each connected to the recorder preferably by a pair of electrode leads L141-L142, L161-L162, L181-L182, respectively. Three electrical paths each defined by a pair of electrodes, a pair of electrode leads and the patient tissues (not shown) constitute three electrode channels 14, 16, 18. As is well known in the art of recording physiological signals, typical recorders can be used with a single pair or multiple pairs of electrodes thereby representing a single or multiple electrode channel configuration. It will, however, become apparent from the following that the invention is equally appropriate for use with various numbers of electrode channels.

The electrodes applied to the patient's body (not shown) are appropriately medical electrodes commonly used in the monitoring and recording of physiological signals. A ground electrode G of a typical variety is also connected to the patient's body (not shown) and to the recorder to establish a reference potential.

Current source 12 of impedance measurement system 20, which is described in more detail below, is connected to electrode channels 14, 16, 18. The impedance of each electrode channels 14, 16, 18, designated Z14, Z16, and Z18 respectively, includes several components. By way of example, the impedance components associated with electrode channel 14 are: impedance Zl141, representing the impedance of a first lead connecting the recorder to a first electrode; impedance Ze141, representing the impedance of the first electrode; impedance Zi141, representing the impedance of a first interface between the first electrode and a first skin area of the patient's body; impedance ZT140, representing the impedance of the patient's internal tissues; impedance Zi142, representing the impedance of a second interface between a second skin area of the patient's body and a second electrode; impedance Ze142, representing the impedance of the second electrode; and impedance Zl142, representing the impedance of a second lead connecting the second electrode to recorder 60. It should be noted that each interface impedance Zi141 and Zi142 also includes two additional interface impedance components associated with the gel and/or adhesive commonly applied to a patient's skin to improve respectively, electrical contact and mechanical bonding between the patient's skin and the electrodes. These two interface components are the electrode-to-gel (and/or adhesive) and gel-(and/or adhesive)-to-skin impedances which for ease of reference have been included in interface impedances Zi141 and Zi142. Similarly, the impedance of the electrical contacts between the output terminals of recorder 60 and each lead, and between each lead and each electrode have not been accounted for separately in the preceding description, but are included in lead impedances Zl141, Zl142 and electrode impedances Ze141, Ze142, respectively.

Current source 12, coupled to electrode channels 14, 16, 18, over lines 41-42, 61-62, 81-82, applies an analog current to each electrode channel. The analog current flowing through each electrode channel impedance Z14, Z16, Z18 generates across each electrode channel a voltage signal which is used to calculate impedance values Z14, Z16 and Z18. A recorder of the present invention conveniently indicates, on recorder display 31, the range in which the electrode channel impedance falls. In addition, a recorder of the present invention validates each impedance measurement by confirming, and indicating as applicable, the electrical integrity of the electrode channel measured, in other words by confirming that there are no lead off or defective wire conditions.

Confirmation of lead integrity is necessary in order to avoid reliance on misleading impedance indication. A misleading impedance indication is possible as an electrically open electrode channel will not be characterized by an electrode channel impedance of infinite value. Rather, the impedance of an electrode channel in such state will more likely appear to have a mid-range value. Impedance measurement system 20 confirms the electrical integrity of electrode channels 14, 16, 18 by sharing pace detect circuitry 50 with pace detect recorder 10. A detailed explanation of how the electrical integrity of each electrode channel is confirmed in accordance with the present invention is given below in the context of the structural and functional descriptions of high range filtering stages 19H, 21H, 23H.

In the preferred embodiment, as represented in FIG. 1, a microprocessor 11 is suitably programmed to generate, for a limited amount of time hereinafter called calibration time, two complementary oscillating voltage signals +IMP D, −IMP D. This calibration time is preferably in the order of a few minutes so as to be sufficient for the attending technician to apply the electrodes to the patient's body and for the recorder to confirm their proper application by measuring the impedance of each electrode channel and confirming electrical integrity. The two oscillating voltage signals +IMP D, −IMP D, which are preferably kept in complementary states in order to avoid undesirable polarization effect of the electrodes, essentially have very short transition times, in the order of a few microseconds. Voltage signals +IMP D, −IMP D, are coupled over lines 32-34, to current source 12. Current source 12 attenuates the signals, filters out high frequency noise, and converts the attenuated and filtered complementary signals into a pair of short transition time complementary oscillating load-independent currents which are independent of the impedance of the electrode channel to which current source 12 is connected. The oscillating load-independent currents are then applied over lines 41-42, 61-62, 81-82, to electrode channels 14, 16, 18 and produce voltage signals V14, V16, V18 across electrode channels 14, 16, 18, respectively. Voltage signals V14, V16, V18 are proportional to the impedance of the respective electrode channels.

The oscillating load-independent currents generated by current source 12 are preferably of limited amplitude but are, however, of sufficient amplitude to create measurable voltages V14, V16, V18. These electrode channel voltages V14, V16, V18 are amplified using recording channel amplification stages 13, 15, 17 of standard recorder 40. Each amplified signal, hereinafter referred to as A14, A16, A18, appearing at the output of amplification stages 13, 15, 17, is respectively coupled, over lines 43, 63, 83, to dual range filtering stages 19, 21, 23, of pace detect recorder 10. Low range sections, referred to as 19L, 21L, 23L, of filtering stages 19, 21, 23, respectively, generate time-dependent signals Vt14, Vt16, Vt18, across resistors 326, 342, 356 respectively. Time-dependent voltage signals Vt14, Vt16, Vt18 cause the output of low range filtering stages 19L, 21L, 23L, to produce timing signals which are applied, over lines 26, 28, 30 to timing inputs P1, P2, P3, of microprocessor 11. A more detailed explanation of the operation of low range filtering stages 19L, 21L, 23L, is provided below in conjunction with the structural and functional description of filtering stages 19, 21, 23.

Microprocessor 11 is programmed to determine the elapsed times between each transition edge of the oscillating load-independent current signals applied to electrode channels 14, 16, 18, and the occurrence of a signal at the output of low range filtering stages 19L, 21L, 23L. From this determination, microprocessor 11 ascertains, preferably using a look-up table, impedances Z14, Z16, Z18 of electrode channels 14, 16, 18. In addition, in response to amplified signals A14, A16, A18, each high range section, referred to as 19H, 21H, 23H, of filtering stages 19, 21, 23, respectively, generates a signal which is indicative of a lead off or defective electrode lead condition, and is applied to appropriate inputs DET1, DET2, CHAN.3 Lead Off, of microprocessor 11 over lines 27, 29, 25 respectively. Thus, the use of an impedance measurement system in accordance with the present invention in conjunction with shared circuitry of a pace detect recorder of a type commonly available, allows reliable determination of electrode channel impedance without requiring a separate piece of equipment.

FIG. 2-5 represent schematic diagrams of a preferred embodiment of a three channel pace detect recorder 10 including the impedance measurement circuitry 20 as illustrated in FIG. 1. It should be noted that, although for ease of understanding the description of the preferred embodiment sometimes makes reference to components specifically associated with electrode channel 14 connected to the first channel input of recorder 60, this description, unless otherwise stated, is similarly applicable to the other two channels 16, 18 of recorder 60.

Figure 2:
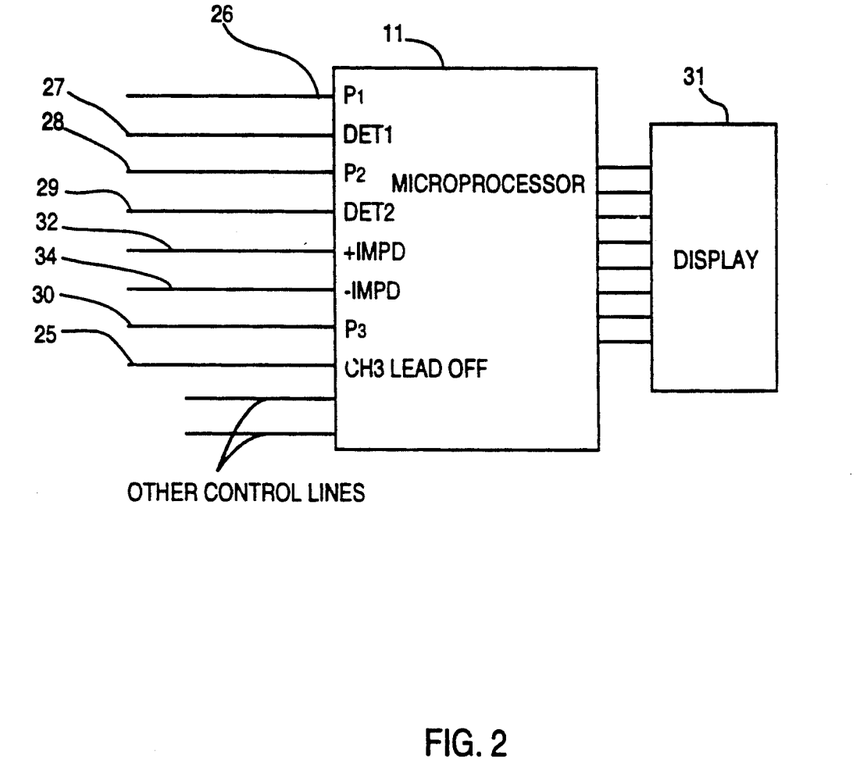
FIGS. 2-5 comprise schematics of the impedance measurement system 20 cooperating with pace detect recorder 10 as described in FIG 1.
Figure 3:
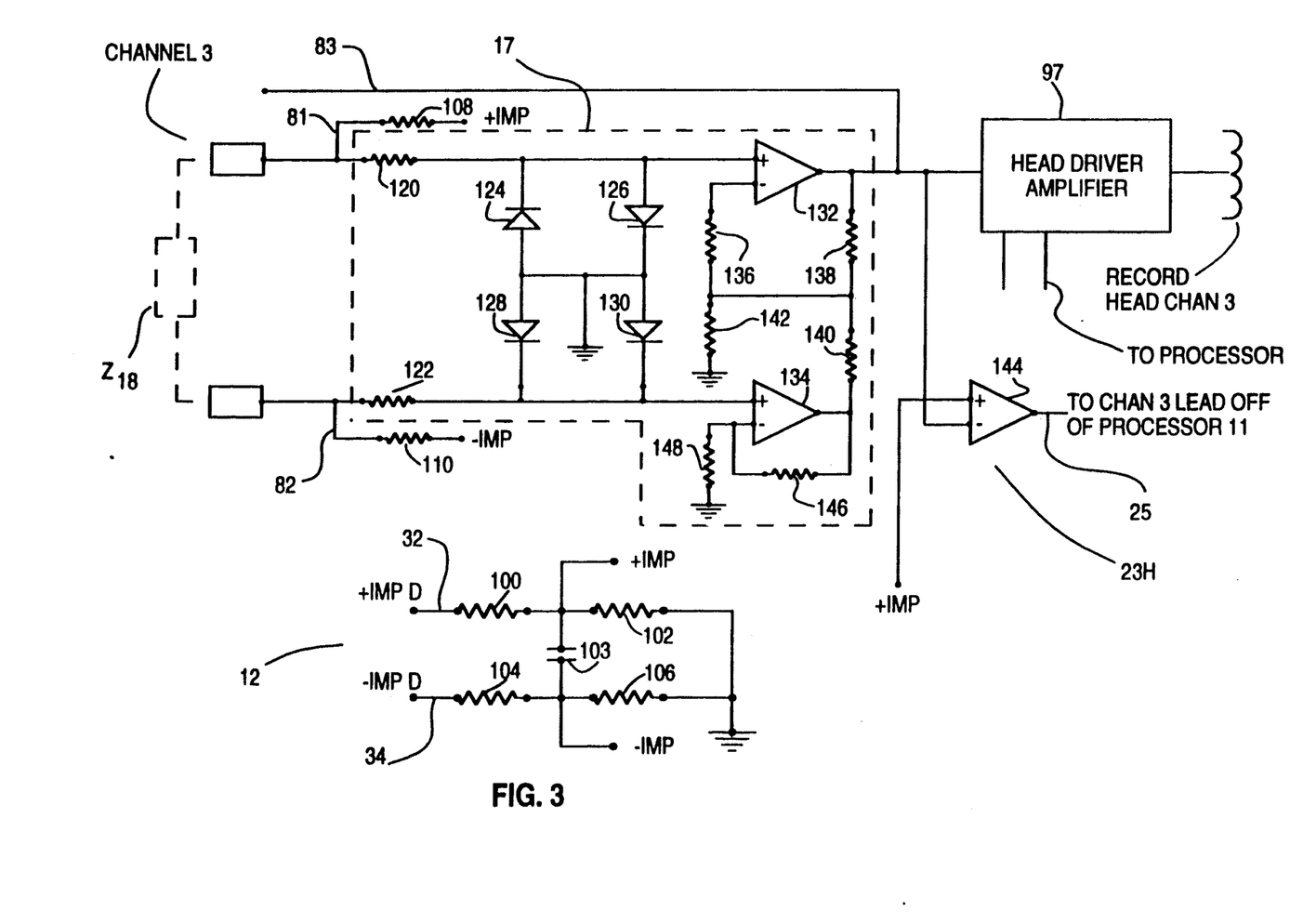
Figure 4:
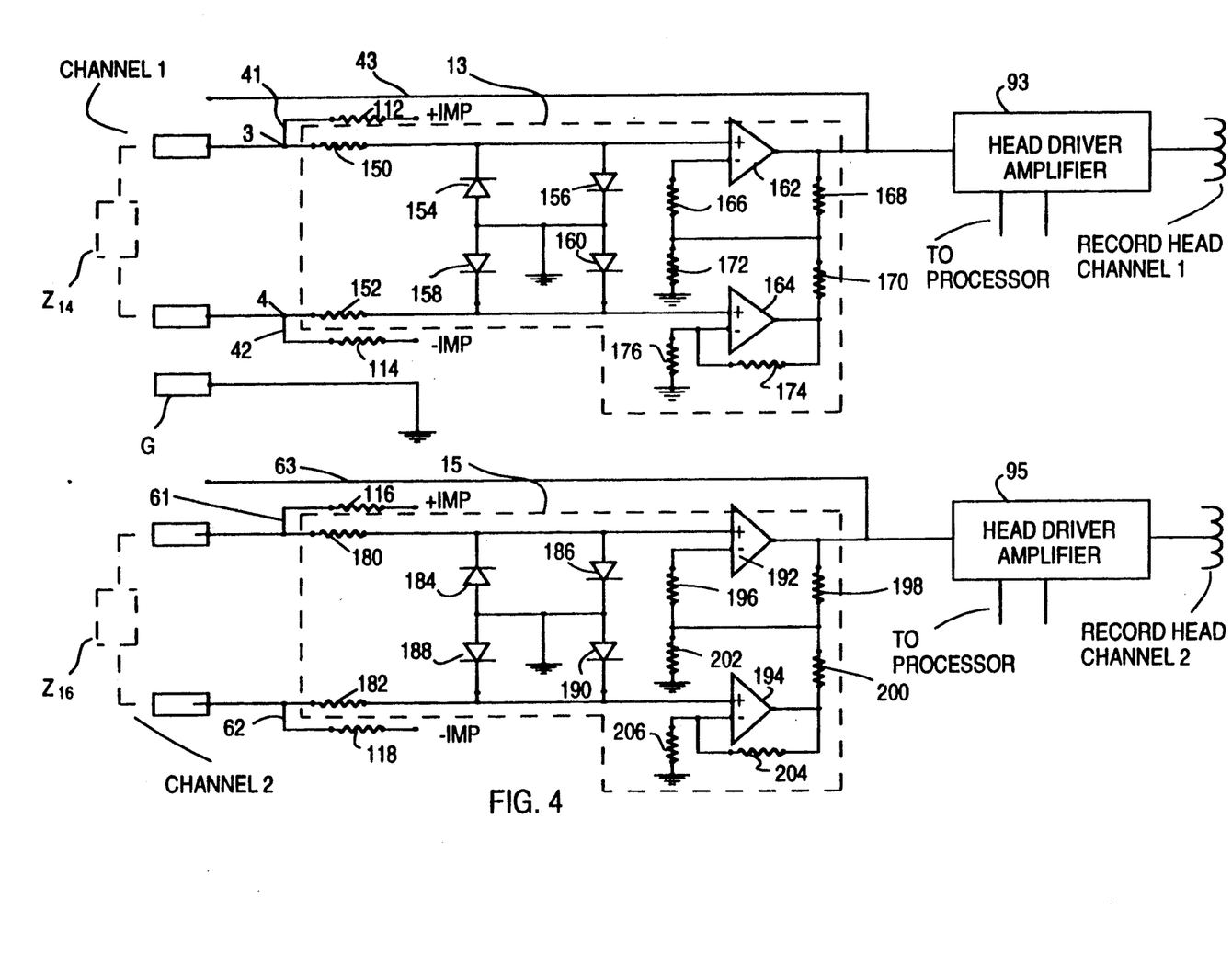

As best illustrated in FIGS. 2, 3 and 4, microprocessor 11 of pace detect recorder 10 includes a conventional 8 bit microprocessor suitably programmed to generate at two complementary outputs, identified as +IMP D and −IMP D, two 4 Hz, short transition time, complementary square waves of amplitude IMP. The complementary outputs of microprocessor 11 are coupled over lines 32, 34, to current source 12. Current source 12 attenuates and filters the short transition time complementary signals to remove high frequency noise and converts these attenuated and filtered signals into a pair of oscillating short transition time load-independent currents. Current source 12 conveniently includes a resistor network and coupled capacitor comprising resistors 100, 102, 104, 106 and capacitor 103 and three pairs of resistors 120-122, 150-152, and 180-182 (FIGS. 3, 4).

The oscillating load-independent currents generated by current source 12 are then applied over lines 41-42, 61-62, and 81-82 to electrode channels 14, 16, 18, respectively, and produce corresponding short transition time voltages V14, V16, V18, across these electrode channels.

For increased sensitivity, and as shown in FIG. 4, it is advantageous to couple current source 12 over lines 41-42 to electrode channel 14 at nodes 3 and 4 where electrode channel leads L141-L142 are connected to recorder 60 rather than through resistors 150, 152 connected in series with the input to recorder 60.

Electrode channel voltages V14, V16, V18 generated across electrode channels 14, 16, 18, by application of the load-independent currents to electrode leads L141-L142, L161-L162, L181-L182, are amplified by amplification stages 13, 15, 17 of standard recorder 40. As best shown in FIGS. 3 and 4, each of amplification stages 13, 15, 17, preferably includes a pair of impedance elements, a diode defibrillator bridge, and a pair of instrumentation amplifiers. By way of example, and as shown in FIG. 4, amplification stage 13 connected to electrode channel 14 comprises impedance elements 150-152, diode defibrillator bridge consisting of diodes 154, 156, 158, 160, instrumentation amplifiers 162 and 164 and associated gain resistors 166, 168, 170, 172, 174.

Instrumentation amplifiers such as 162, 164 are typically characterized by high input impedance value so that substantially all of the load-independent current flows through electrode channel 14 with a very limited amount being diverted to the input stage of instrumentation amplifiers 162, 164. Moreover, as instrumentation amplifiers such as 162, 164 also typically have a high common mode rejection ratio, amplification stages 14, 16, 18, generate short transition time signals A14, A16, A18 proportional to electrode channel voltages V14, V16, V18, respectively, while also effectively rejecting the common mode signal appearing at electrode leads L141-L142, L161-L162, L181-L182 connected to the recorder 60.

Figure 5:
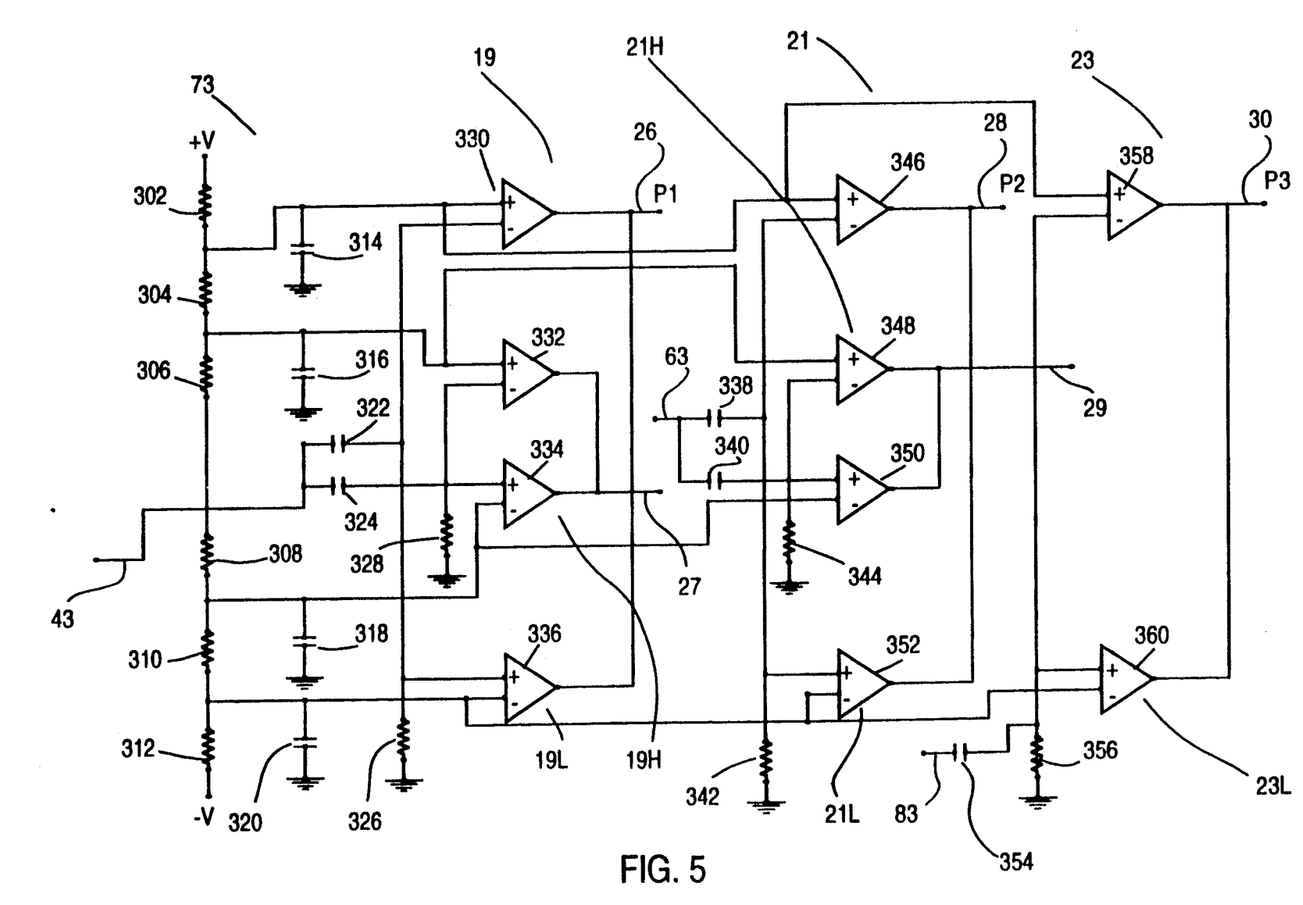

As best illustrated in FIGS. 3, 4 and 5, amplified signals, A14, A16, A18, at the outputs of stages 13, 15, 17, are then coupled over lines 43, 63, 83 respectively, to dual range filtering circuits 19, 21, 23 of pace detect recorder 10. The functional description of dual range filtering circuits 19, 21, 23 is described in more details below. Dual range filtering stages 19, 21, 23 preferably include low range stages identified as 19L, 21L, 23L and high range stages 19H, 21H, 23H respectively.

Low range filtering stages 19L, 21L, 23L, cooperating with electrode channels 14, 16, 18 respectively, are identically constructed. By way of example and referring to electrode channel 14, low range filtering stage 19L includes capacitor 322 and resistor 326, which are preferably chosen to establish a 10 millisecond time constant, and comparators 330, 336 (FIG. 5). Comparators 330 and 336, the inverting and non-inverting inputs of which are respectively coupled to the common point between capacitor 322 and resistor 326 are used for impedance measurement of electrode channel 14.

High range filtering stage 19H includes capacitor 324 and resistor 328, which may preferably be selected to achieve a 220 microsecond time constant, and comparators 332, 334 (FIG. 5). Comparators 332 and 334, the inverting and non-inverting inputs of which are respectively coupled to the common point between capacitor 324 and resistor 328, are used to determine the integrity of electrode leads L141-L142. This exact structural description also applies to high range filtering stage 21H which cooperates with electrode channel 16 to determine the integrity of electrode leads L161-L162. For reasons which will be explained below, high range filtering stage 23H, includes comparator 144 (FIG. 3), which is used to determine the integrity of electrode leads L181-L182 of electrode channel 18.

A resistor ladder 73, including resistors 302, 304, 306, 308, 310, 312 connected in series and filtering capacitors 314, 316, 318, 320, is coupled between the positive and negative power supply rails, referred to as +V, −V, of pace detect recorder 10. Resistor ladder 73, as shown in FIG. 5, is tapped to establish threshold voltages. More specifically, +V is coupled to the non-inverting inputs of comparators 330, 346, 358 through resistor 302 to establish threshold voltages V330, V346, V358 respectively and to the non-inverting inputs of comparators 332, 348, through resistors 302 and 304 to establish threshold voltages V332, V348 respectively. −V is coupled to the inverting inputs of comparators 334, 350 through resistors 312, and 310, to establish threshold voltages V334, V350 respectively and to the inverting inputs of comparators 336, 352, 360 through resistor 312 to establish threshold voltages V336, V352, V360 respectively.

As best illustrated in FIG. 5 and referring to electrode channel 14, since complementary voltage signals +IMP D, −IMP D generated by microprocessor 11 and all other oscillating signals derived from complementary voltage signals +IMP D, −IMP D, such as V14 and amplified signals A14 connected to the input of dual range filtering stage 19, are characterized by a short transition time, at each transition, hereinafter called assertion time, of the oscillating current signals generated by current source 12 and applied to electrode channel 14, comparators 330, 336 of low range filtering stage 19L are asserted.

As explained in connection with FIG. 1, amplified signal A14 is generated in response to electrode channel voltage V14 which is itself dependent on electrode channel impedance Z14. Signal A14 applied to RC network 322-326, generates time-dependent voltage Vt14 across resistor 326 (FIG. 5). Time-dependent voltage V14 which is applied to the inverting and non-inverting inputs of comparators 330 and 336 respectively, is compared to threshold voltage V330, V336 established by resistor ladder 73. Accordingly, the instant at which time-dependent voltage Vt14 drops below threshold voltages V330, V336 depends upon the amplitude of signal A14, and consequently upon the characteristics of electrode impedance Z14. At the instant where time-dependent voltage Vt14 drops below threshold voltages V330, V336, this instant being hereinafter referred to as reset time, comparators 330, 336 return to their nonasserted states and provide an output signal via line 26 to timing input P1 of microprocessor 11.

Microprocessor 11 calculates the time elapsed between each assertion and reset times, in other words between each transition of the oscillating current signals applied to electrode channel 14 and the return to a nonasserted state of comparators 330 and 336. Since as explained directly above, the instant at which comparators 330, 336 return to their nonasserted states depends upon the time it takes for time-dependent voltage Vt14 to drop below threshold voltages V330, V336, and since the original amplitude of decaying voltage Vt14 depends on the value of electrode impedance Z14, determination by microprocessor 11 of the elapsed time between assertion and reset times generates the representative value of impedance Z14 of electrode channel 14.

By way of example only, an elapsed time of 20 milliseconds may indicate an impedance value of 50,000 ohms, whereas an elapsed time in the range of 70 to 100 milliseconds may evidence an inadequately applied electrode.

It should be noted that although in the description of the preferred embodiment comparators 330 and 336 return to a nonasserted state as a result of time-dependent voltage Vt14 across resistor 326 dropping below threshold voltages V330, V336, it is understood that the principle of the present invention remains the same whether comparators 330 and 336 return to nonasserted state as a result of time-dependent voltage Vt14 approaching and crossing the threshold levels from an increasing or decreasing direction.

The functional description of low range section 19L of dual range filtering stage 19 in conjunction with electrode channel 14 is similarly applicable to low range sections 21L, 23L of dual range filtering stages 21 and 23 which cooperate with electrode channels 16 and 18 respectively to determine impedances Z16, Z18 of these electrode channels.

High range filtering stages 19H, 21H, of dual range filtering stages 19, 21, are used in a manner generally known to those skilled in the art to generate a pace detect signal for electrode channels 14 and 16 respectively. High range filtering stages 19H, 21H, include respectively, capacitor 324, resistor 328, cooperating with comparators 332-334 and capacitor 340, resistor 344 cooperating with comparators 348-350 (FIG. 5). High range filtering stages 19H, 21H are also used to verify the integrity of leads L141-L142 and L161-L162.

By way of example, and referring to channel 14, as explained in connection with the structural description of high range filtering stage 19H, RC network 328-324 of stage 19H establishes a very short time constant, in the order of 220 microseconds (FIG. 5). Accordingly, if electrode channel 14 is electrically in an open condition, (i.e., electrode lead L141 or L142 is not connected or is broken, or electrode X1 or X2 is defective), the short transition time signal coupled over line 43 to the input of high range filtering stage 19H passes through RC network 324-328 and causes comparators 332-334, which are normally maintained in an unasserted state by threshold voltages V332, V334, to leave that state and reach saturation. The signal which appears at the outputs of comparators 332-334 as a result of this change of states is sent to input DET1 of microprocessor 11.

Conversely, if electrode channel 14 is not electrically open, the characteristics of electrode channel impedance Z14 will significantly lengthen the rise time of signal A14 appearing on line 43. As a result, no signal will pass through high pass filter network 324-328 and comparators 332-334 will remain in unasserted states. Processing by microprocessor 11 of the impedance measurement and lead integrity signals allows validation of measured electrode channel impedance Z14.

Since pace detect recorder 10 of the type used with impedance measurement system 20 does not require a pace detect capability for electrode channel 18, verification of lead integrity for electrode channel 18 is achieved by high range stage 23H which includes comparator 144 (FIG. 3) being connected to an appropriate input of microprocessor 11. More specifically, amplified signal A18 and attenuated oscillating voltage signal +IMP are connected respectively to the inverting and non-inverting inputs of comparator 144. If electrode channel 18 is electrically in an open condition, (i.e., electrode lead L181 or L148 is not connected or is broken, or electrode Z1 or Z2 is defective), the amplitude of signal A18 will be much greater than +IMP since an open channel condition drives instrumentation amplifiers 132, 134 to saturation. The resulting signal appearing at the output of comparator 144 is then applied to "channel 3 lead off" input of microprocessor 11 to validate the measured value of impedance Z18 of electrode channel 18.

It should also be noted that the lead off detection provided by comparator 144 also allows recorder 60 to determine automatically whether two or three sets of electrodes are connected to the patient. In other words, it is not necessary for the attending technician to manually select the mode of operation of recorder 60. That is, based on the status of the "channel 3 lead off" input, recorder 60 determines automatically whether the recorder is being connected to the patient's body to operate as a three channel recorder or as a two channel recorder with pace detect capability.

A flow chart of the software utilized to control the operation of microprocessor 11 is illustrated in FIG. 6A-6E. As indicated above in conjunction with the description of FIG. 1, microprocessor 11 executes during the calibration time an impedance measurement routine allowing recorder 60 to determine whether electrodes X1-X2, Y1-Y2, Z1-Z2 are correctly applied to the patient's body and to confirm electrical integrity of electrode channels 14, 16, 18.

Figure 6A:
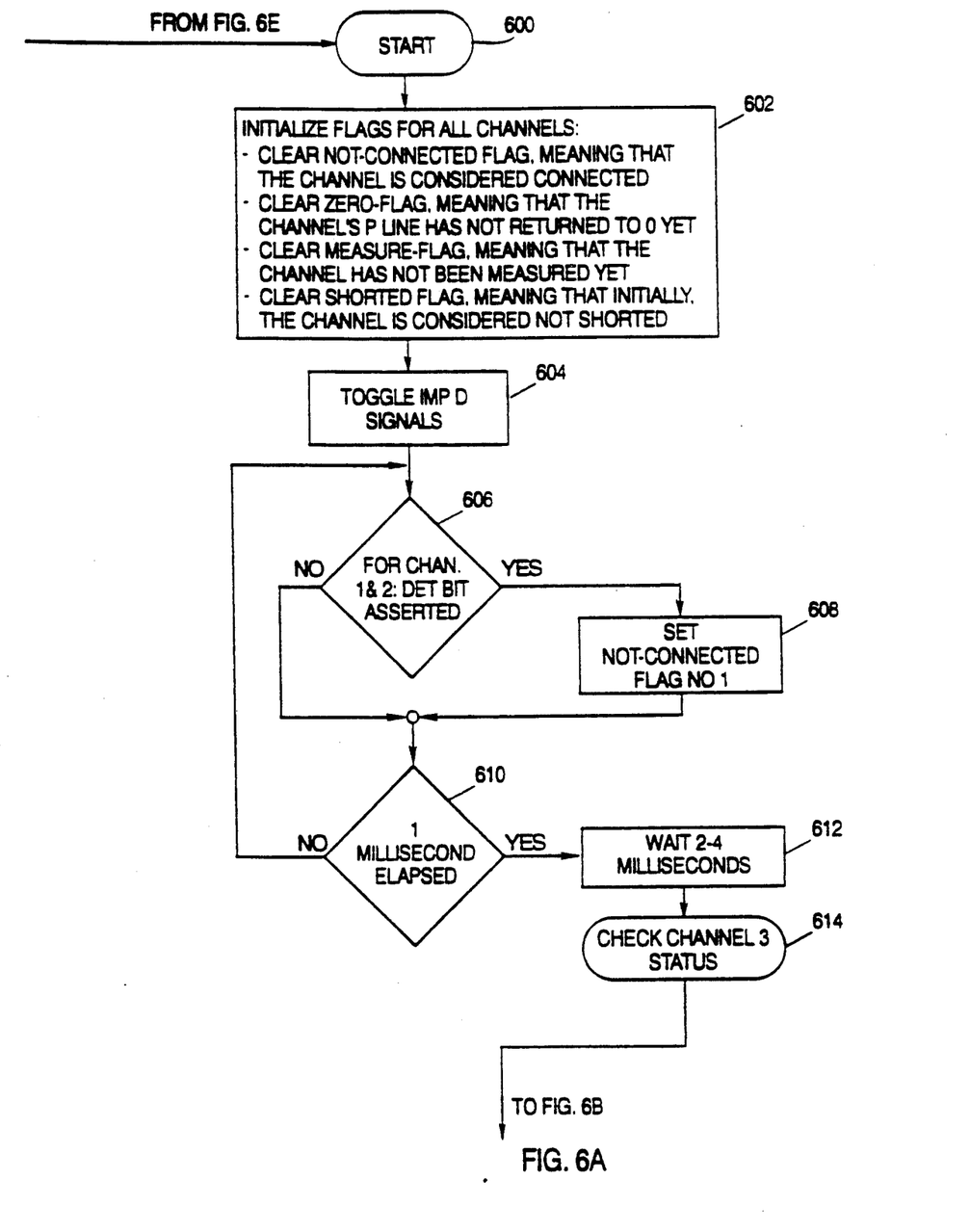
FIGS. 6A-6E represents a flow chart of the software utilized to program microprocessor 11 used in impedance measurement system 20.
Figure 6B:
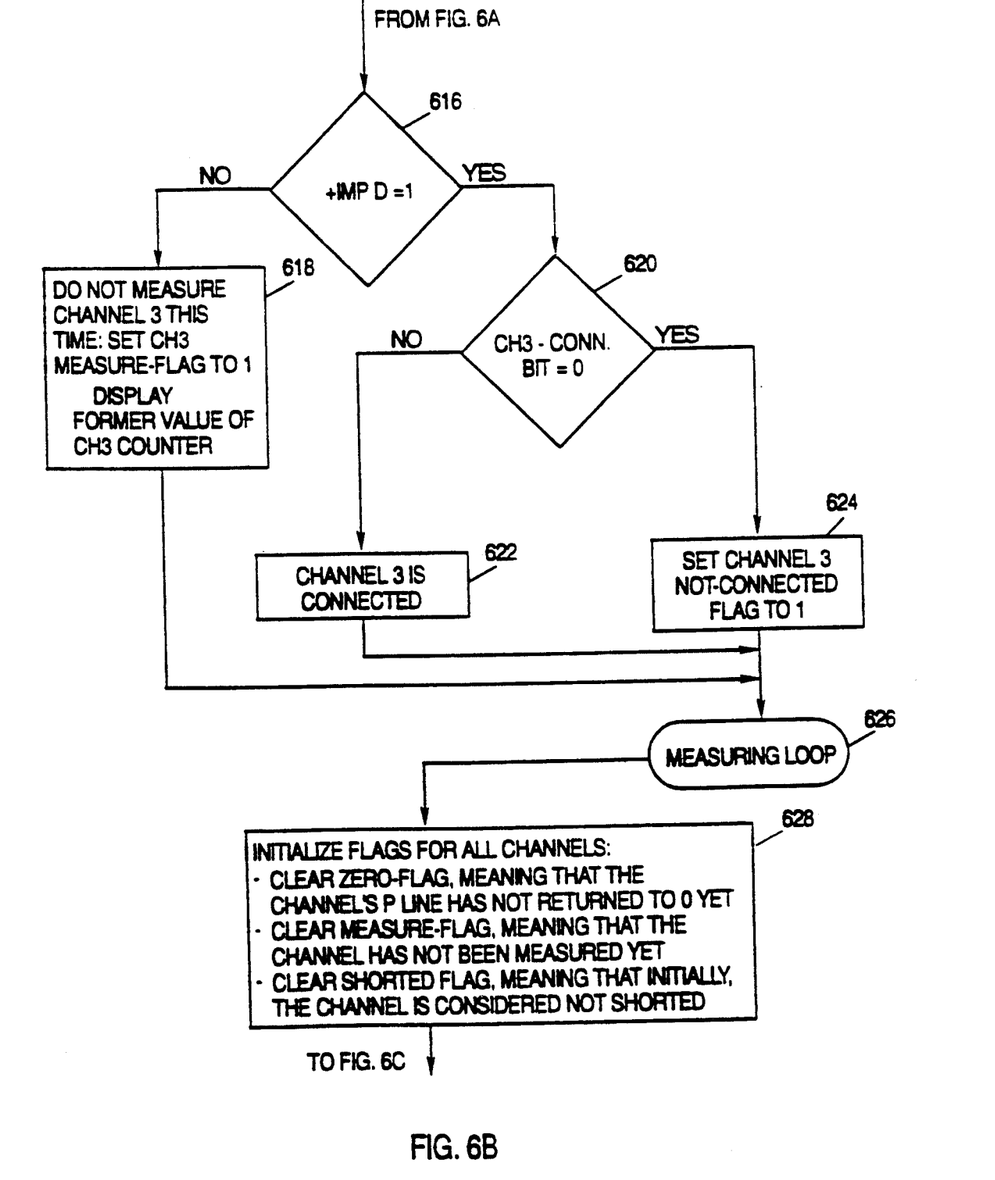

The impedance measurement routine starts at 600 (FIG. 6A). The program then initializes all flags for all channels (step 602) of microprocessor 11. More specifically, first microprocessor 11 "channel 3 lead off", DET1, DET2 flags are cleared. These flags allow processor 11 to verify the electrical integrity of all three electrode channels. Then, microprocessor 11 zero-flags are cleared to zero A microprocessor 11 zero-flag associated with a particular channel is one which indicates that that particular channel has not returned to logical 0. In other words, this means that the pair of comparators, of the low range filter associated with that particular channel, e.g., comparator pair 330-336 of channel 1 (FIG. 5), has not returned to its asserted state. Then, microprocessor 11 channel-measured flags are also cleared to indicate that the impedance of these electrode channels has not been measured. Finally, the channel-shorted flags of microprocessor 11 are also cleared to establish that, initially each channel is considered not to be in an electrical short condition.

Outputs +IMP D and −IMP D of microprocessor 11 are then toggled (step 604) to generate complementary oscillating voltage signals characterized by short transition times. It is then determined for channels 1 and 2 whether the microprocessor 11 inputs identified as DET1 and DET2, connected to the output of high range filters 19H, 21H respectively, are asserted (step 606). Step 606 in other words determines whether comparators 332, 334, 348, 350 (FIG. 5), have been asserted. If so, microprocessor 11 "not connected" flag is set to 1 (step 608) and the program pauses for one millisecond (step 610). During that one millisecond, the program loops back to step 606. After one millisecond has elapsed, the program pauses for an additional two to four milliseconds (step 612) and then enters a subroutine to check the status of channel 3 (step 614).

To determine the status of channel 3, the program determines whether +IMP D is at logical one (step 616, FIG. 616), in other words whether a +IMP signal is applied to the non-inverting input of comparator 144. If so, processor 11 then determines whether channel 3 is connected (step 620). If channel 3 is not connected, comparators 132, 134 (FIG. 3), will go to saturation and a high level voltage will be applied to the inverting input of comparator 144 (FIG. 3). As a result, the output of comparator 144 will go low. This logical zero signal, which is connected to the channel 3 lead off input of processor 11, will indicate that channel 3 is not connected by setting the channel 3 not-connected flag to one (step 624). The program then enters the impedance measuring loop at step 626. Conversely, if microprocessor 11 determines at step 620 that channel 3 is connected, channel 3 not-connect flag will not be set and microprocessor 11 enters the measuring loop at step 626.

Referring back to step 616, if +IMP D is at logical 0, in other words if no +IMP signal is applied to the non-inverting input of comparator 144, microprocessor 11 is instructed not to determine whether channel 3 is connected at this time. Microprocessor 11 is also instructed to set channel 3 measured-flag to one and to continue displaying the former impedance value Z18 for channel 3 (step 618). The program then enters the measuring routine at step 626.

Before measuring the impedance of each electrode channel, the program initializes all flags for all channels (step 628) of microprocessor 11. More specifically, first microprocessor 11 zero-flags are cleared to zero. As indicated above in connection with step 602 (FIG. 6A), a zero-flag associated with a particular channel is one which indicates that that particular channel has not returned to logical 0. Then, microprocessor 11 channel-measured flag is also cleared to indicate that the impedance of the electrode channel has not been measured. Finally, the channel-shorted flag of microprocessor 11 is also cleared.

Figure 6C:
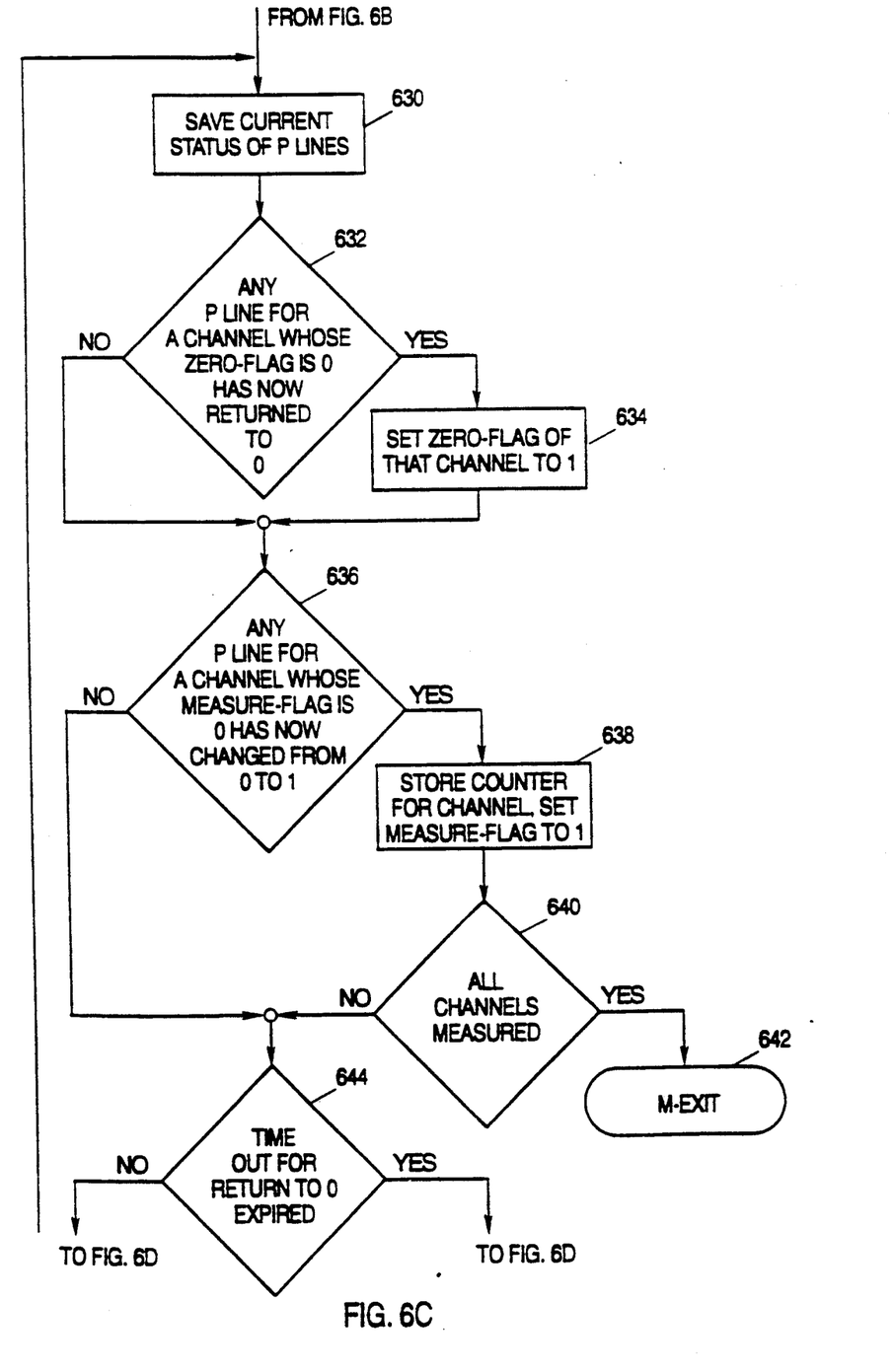
Figure 6D:
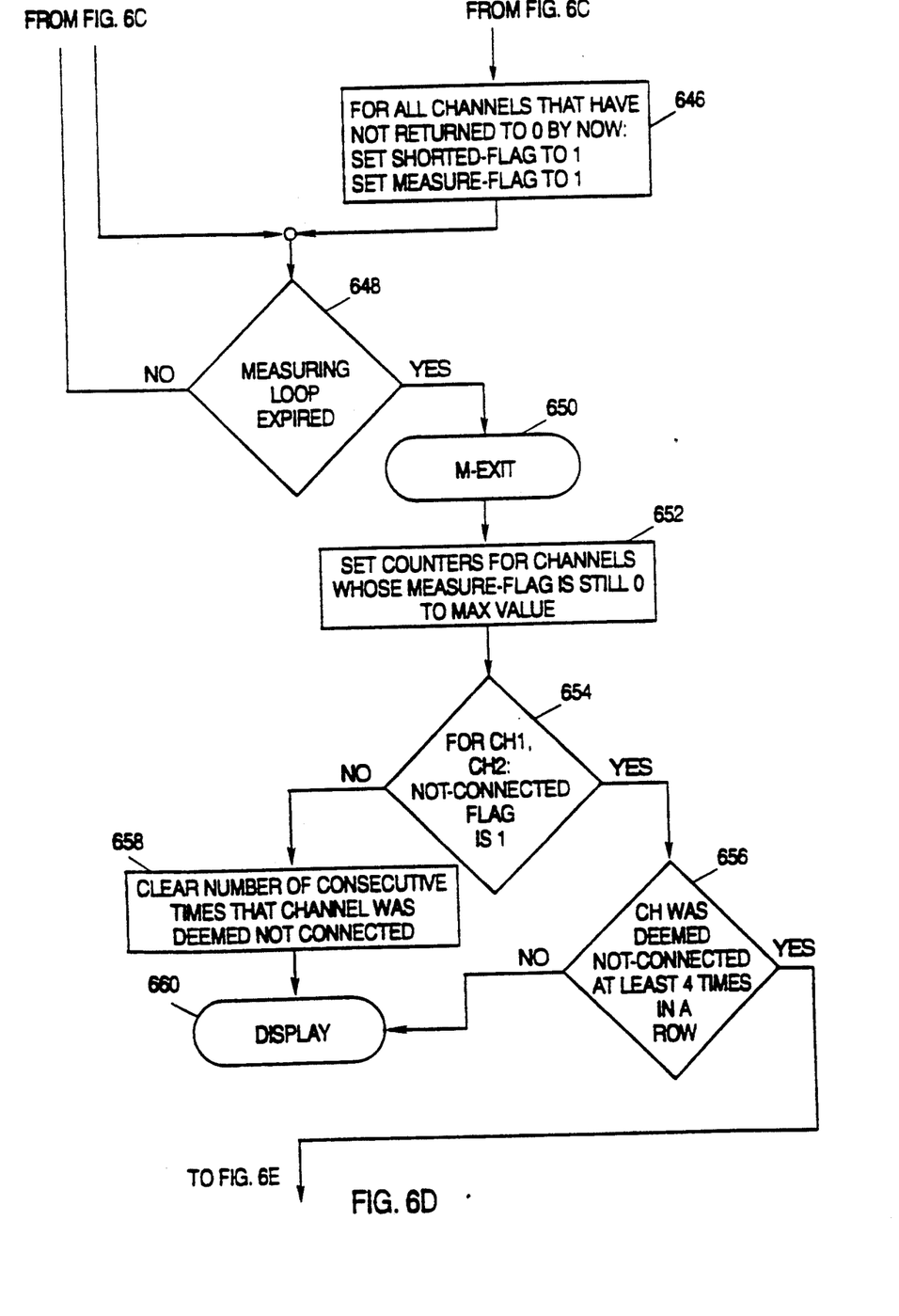

The current status of lines 26, 28, 30 connected to microprocessor 11 inputs P1, P2, P3 respectively, is then saved (step 630, FIG. 6C). The program then determines whether at any time during this loop comparators 330, 336, 346, 352, 358, 360 have been asserted at least once. This allows a determination of whether the particular channel is in an electrical short condition as a channel in this condition will not allow comparators of the low range filtering stage cooperating with that particular channel to be asserted. Whether the channel is shorted is indicated for each channel by determining whether the zero-flag of microprocessor 11 has returned to zero (step 632). If so, the zero-flag is set to one (step 634) indicating a channel shorted condition.

The program then determines for each channel whether the channel has been measured. This is achieved by microprocessor 11 determining, for each channel whose measure-flag is zero, whether the status of that measure-flag has changed from zero to one (step 636). If not, which indicates that that particular channel has not yet been measured, the program proceeds to determine at step 644 whether the time delay of at least 117 milliseconds has expired. If that time delay has not yet expired, processor 11 inquires further at step 648 (FIG. 6D), whether the time allocated for the entire measuring loop has expired. If not, processor 11 loops back to step 630 (FIG. 6C), and repeats steps 630 to 644.

Referring back to step 636 (FIG. 6C), if the measure-flag indicates that the particular channel has been measured, processor 11 stores the content of the counter which has measured the time interval between the assertion time and the reset time and sets the measure-flag to one (step 638). Once processor 11 determines at step 640 that all channels have been measured, processor 11 exits the measuring loop (step 642). If, however, processor 11 determines that not all channels have been measured, the program will keep processor 11 in the measuring loop and repeat steps 644, 648 before returning to step 630.

Referring back to step 640, if processor 11 determines that not all channels have yet been measured and also determines, at step 644, that the time delay has expired, processor 11 sets the measure-flag to one and the shorted-flag to one (step 646, FIG. 6D) to indicate an error condition. This is because a time delay which expires before the P input of processor 11 could go from a nonasserted to an asserted state and return to a nonasserted state indicates that the electrode channel is in an electrical short condition. Processor 11 will, however, keep verifying this condition until the time allocated for the measuring loop has expired (step 650).

After processor 11 exits the measuring loop at step 650, for all channels which indicate that they have not been measured, the program sets the counters to maximum value (step 652). This is because if during the measuring routine processor 11 neither found these channels shorted nor could processor 11 measure the time interval between an asserted time and a reset time and store this information in the corresponding counters, this indicates that the impedance of the particular electrode channel is too high for reliable recording of physiological signals.

In preparation to display the impedance value or the error status of each electrode channel the program then proceeds to determine whether for channels 1 and 2 the channel not-connected flag is one (step 654). If not, the counter which may have registered the information regarding how many consecutive times the channel was not connected is cleared (step 658). Then the impedance value of the electrode channel is displayed (step 660). If for channel 1 or 2, the channel not-connected flag indicates that the particular channel was found not connected (step 654), processor 11 then determines whether this not-connected status was confirmed at least four consecutive times (step 656). If not, the status of the particular electrode channel is displayed (step 660).

Figure 6E:
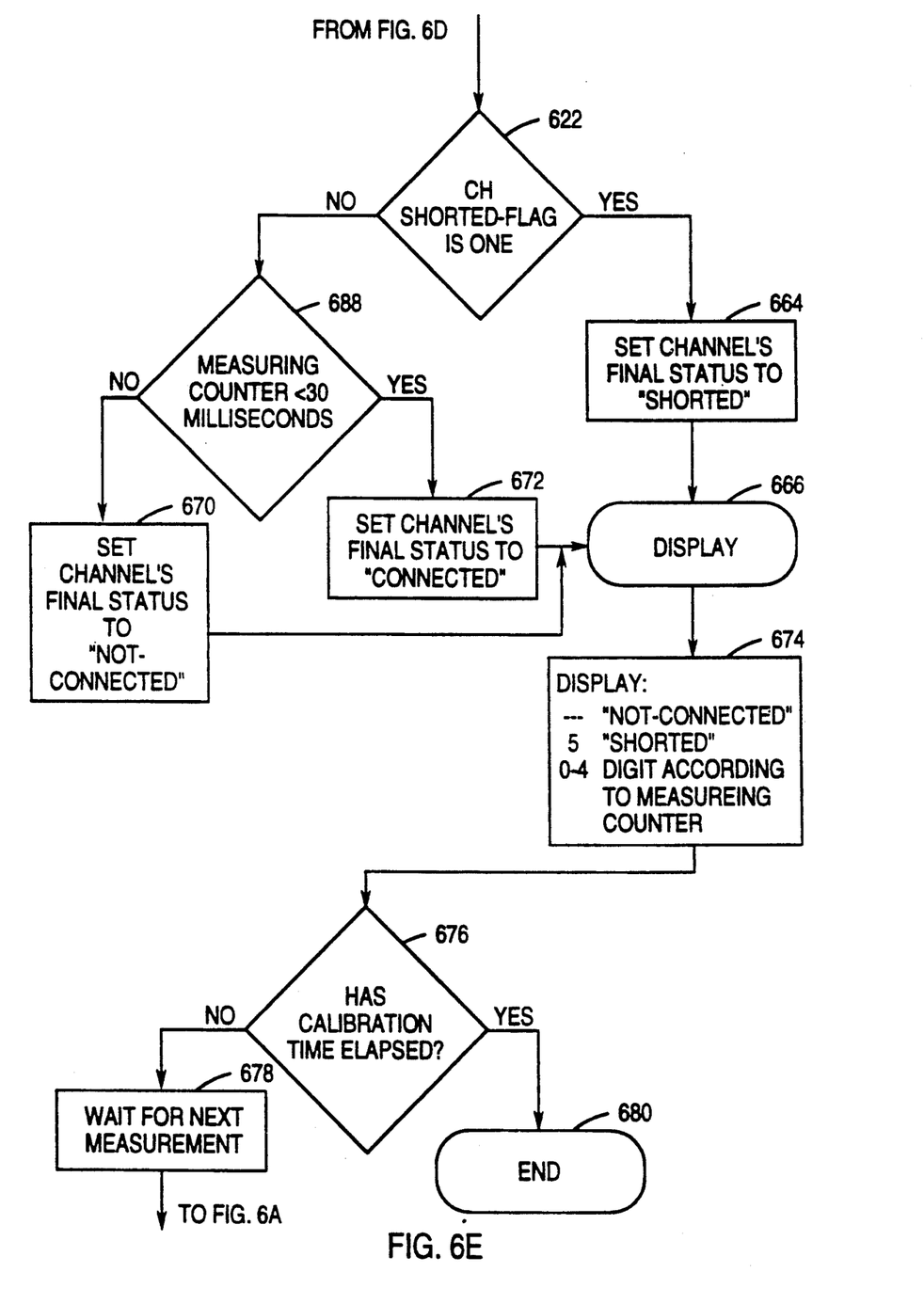

Conversely, if processor 11 determines that either channel 1 or channel 2 has been found not-connected at least four consecutive times (step 656), the program proceeds to determine whether processor 11 has also already established that that particular channel is in addition shorted (step 662, FIG. 6E). If so, the status of the particular channel is set to shorted (step 664) and this information is displayed (step 666).

Referring back to step 662, if, however, processor 11 determines that that particular channel is not shorted, processor 11 ascertains whether the time interval between an asserted and a reset time, as indicated by the content of the counter associated with the particular channel, is less than 30 milliseconds (step 668). If so, the status of the particular channel is set to connected (step 672) and recorder 60 displays (step 666) the impedance value of the electrode channel by matching, in a look-up table, the content of the counter to an impedance value. If the time interval between an assertion time and a reset time is greater than 30 milliseconds (step 668), the status of the particular channel is set to not-connected (step 670) and this information is displayed (step 666).

Processor 11 displays the impedance or the electrical status of a particular electrode channel in one of the following manners (step 674):

"- - -" to indicate a channel not-connected;

"S" to indicate a channel in a shorted condition;

"0", or "1", or "2", or "3", or "4", as obtained from a look-up table and according to the value of the time interval measured by processor 11 and stored in the counter. Once the status of all electrode channels is displayed, processor 11 determines whether the calibration time has elapsed, (step 676). If not, processor 11 waits for the next measurement (step 678) and then loops back to the beginning of the impedance measurement routine (step 600). If the calibration time has elapsed (step 676), processor 11 exits the calibration mode at step 680.

As was explained earlier in connection with the functional description of the dual range filtering stages circuitry, it can be appreciated that by making microprocessor 11 go through steps 620 and 654 to confirm that the particular channel was found connected, the recorder will not display the impedance measurement without first validating that information.

The preceding description of a preferred exemplary embodiment is provided merely for illustrative purposes, and the invention should not be limited to the specific form shown. For example, other methods of generating load-independent current, from complementary oscillating signals generated by the pace detect circuitry, may be used. Similarly, other timing circuitry may be designed to generate a signal representative of the electrode channel impedance and to measure the elapsed time indicative of that impedance. Moreover, technological advances in the development of system components may make available components which can more effectively carry out the functions of the system. This increased efficiency may be achieved by replacing hardware logic with programmed processing hardware or programmed processing hardware, such as microprocessor 11, with hardware logic.

What is claimed is:

1. An impedance measurement system for measuring impedance of at least one electrode channel for use in a recorder of signals comprising:
    means for generating complementary oscillating signals, said complementary oscillating signals defining at each transition of said oscillating signals an assertion time, said recorder having at least one pair of electrodes, said at least one pair of electrodes being connectably applied to a subject's body, said subject's body and said at least one pair of electrodes defining said at least one electrode channel, said at least one electrode channel cooperating with said means for generating complimentary oscillating signals to monitor and record said signals;
    conditioning means for producing a pair of attenuated and filtered complementary oscillating signals based upon the complementary oscillating signals;
    signal generating means for converting said pair of attenuated and filtered signals into oscillating load-independent currents and applying said oscillating load-independent currents to said electrode channel to produce a responsive signal representative of impedance of said electrode channel;
    amplification and filtering stage means for amplifying and filtering said responsive signal for generating a time-dependent signal;
    threshold means for ascertaining a reset time at which said time-dependent signal crosses a threshold level;
    timing means for measuring a time interval between said assertion time and said reset time; and
    converting means for converting said time interval into an impedance value.

2. The impedance measurement system of claim 1 wherein said conditioning means includes a resistor-capacitor network.

3. The impedance measurement system of claim 2 wherein said signal generating means includes a pair of resistors connectable to said electrode channel.

4. The impedance measurement system of claim 1 wherein said complementary oscillating signals are generated by a microprocessor.

5. The impedance measurement system of claim 1 wherein said complementary oscillating signals have a frequency, and the frequency of said complementary oscillating signals is in a range of signals recorded by said recorder to approximate the impedance of said electrode channel during said monitoring and recording by said recorder of said signals.

6. The impedance measurement system of claim 1 wherein said amplifying and filtering stage means comprises:
    low range filtering stage means for generating said time-dependent signal in response to said responsive signal; and
    high range filtering stage means for generating a signal indicative of electrical integrity of said electrode channel.

7. The impedance measurement system of claim 6 wherein said threshold means for ascertaining said reset time comprises:
    a resistor network to establish threshold levels; and
    a pair of comparators which are asserted at said each transition of said complementary oscillating signals and which return to nonasserted state at said reset time.

8. A method to selectively measure impedance of at least one pair of electrodes, said at least one pair of electrodes being operatively connected to a subject's body, said subject's body and said at least one pair of electrodes defining an electrode channel, comprising the steps of:
    producing complementary oscillating load-independent current signals defining at each transition of said oscillating current an assertion time;
    applying said current signals to said electrode channel;
    monitoring a first voltage produced by the application of said current signals to said electrode channel;
    amplifying and filtering said first voltage to obtain a time-dependent voltage;
    establishing a DC threshold voltage;
    comparing said time-dependent voltage to said threshold voltage to generate, at a reset time, a timing signal indicative of a point at which said time-dependent voltage crosses said threshold voltage;
    measuring a time interval between said assertion time and said reset time;
    converting said time interval to an impedance value; and
    displaying said impedance value.

* * * * *